United States Patent [19]
Rubin et al.

[11] Patent Number: 5,418,366
[45] Date of Patent: May 23, 1995

[54] IR-BASED NITRIC OXIDE SENSOR HAVING WATER VAPOR COMPENSATION

[75] Inventors: Lane H. Rubin, Santa Barbara; Michael D. Jack, Goleta, both of Calif.

[73] Assignee: Santa Barbara Research Center, Goleta, Calif.

[21] Appl. No.: 239,151

[22] Filed: May 5, 1994

[51] Int. Cl.⁶ ................. G01N 21/17; G01N 21/25; G01N 21/03
[52] U.S. Cl. ................. 250/338.5; 250/339.09; 250/339.13; 250/343; 356/438; 356/439
[58] Field of Search ........... 250/338.5, 339.09, 339.13, 250/343, 252.1 A, 252.1 R; 356/438, 439, 246

[56] References Cited

U.S. PATENT DOCUMENTS

| | | | |
|---|---|---|---|
| 4,204,768 | 5/1980 | N'Guyen | 356/439 X |
| 4,560,873 | 12/1985 | McGowan et al. | 250/343 X |
| 4,632,563 | 12/1986 | Lord, III | 250/338.5 X |
| 4,924,095 | 5/1990 | Swanson, Jr. | 250/338.5 |
| 5,210,702 | 5/1993 | Bishop | 364/496 |
| 5,252,828 | 10/1993 | Kert et al. | 250/338.5 X |
| 5,319,199 | 6/1994 | Stedman et al. | 250/339.13 X |
| 5,332,901 | 7/1994 | Eckles et al. | 250/343 X |

OTHER PUBLICATIONS

Article entitled "Analytical Approach—IR Long-Path Photometry: A Remote Sensing Tool for Automotive Emissions:," by G. Bishop et al., in Analytical Chemistry 1989, 61, 617A.

Publication Entitled "Find And Fix The Polluters", by James E. Peterson et al., Chemtech, Jan. 1992, pp. 47–53.

*Primary Examiner*—Constantine Hannaher
*Assistant Examiner*—Edward J. Glick
*Attorney, Agent, or Firm*—W. C. Schubert; W. K. Denson-Low

[57] ABSTRACT

A system (10) for detecting nitric oxide (NO) within an exhaust plume (14) includes a source (18) for generating an optical beam (20) and for directing (22, 24) the optical beam through the exhaust plume, the optical beam having wavelengths within a predetermined band of wavelengths within the infrared (IR) radiation spectrum. The system includes a sensor (32)/filter (30) assembly having a first channel for determining a measured NO transmission value for a first predetermined band of wavelengths; a second channel for determining a measured water transmission value for a second predetermined band of wavelengths; a third channel for determining a measured reference transmission value for a third predetermined band of wavelengths selected so as not to be significantly absorbed by the exhaust plume; and a fourth channel for determining a measured combustion by-product transmission value for a fourth predetermined band of wavelengths. A data processor (38) is responsive to the outputs of the channels for determining an effective NO transmission value from the measured NO transmission value that is scaled by (a) the measured water transmission value, (b) a predetermined factor that compensates for absorption by water within the first predetermined band of wavelengths, and (c) the reference transmission value. The data processor is further operable for converting the effective NO transmission value to a relative NO concentration value using a predetermined calibration factor and for converting the relative NO concentration value to an actual NO concentration value utilizing the measured combustion by-product transmission value.

24 Claims, 8 Drawing Sheets

IR-BASED NITRIC OXIDE SENSOR HAVING WATER VAPOR COMPENSATION

FIELD OF THE INVENTION

This invention relates generally to sensors responsive to specified chemical species and, in particular, to an optical sensor for detecting a concentration of nitric oxide (NO) in an emission from a vehicle, a smokestack and the like.

BACKGROUND OF THE INVENTION

Environmental pollution is a serious problem which is especially acute in urban areas. A major cause of this pollution is exhaust emissions from automotive vehicles. Official standards have been set for regulating the allowable amounts of pollutants species in automobile exhausts, and in some areas, periodic inspections or "smog checks" are required to ensure that vehicles meet these standards.

However, there are still large numbers of vehicles operating on public highways which fail to comply with the standards. It has also been determined that a disproportionately large amount of pollution is generated by a relatively small number of vehicles.

Highly polluting vehicles can operate even in areas in which periodic emission inspections are required. Some older vehicles and special types of vehicles are exempt from inspections.

Anti-pollution devices which are required equipment on newer vehicles accomplish their intended purpose of reducing pollution in the vehicle exhaust to within prescribed levels. However, it is perceived by some vehicle owners that antipollution equipment reduces engine performance.

For this reason, some vehicle owners with mechanical expertise can perform whatever servicing is necessary to place their vehicles in condition to pass required inspections, and subsequently remove anti-pollution devices and/or return the vehicles with an attendant increase in pollutant emissions for normal use.

An anti-pollution program which depends entirely on mandatory periodic inspections performed at fixed facilities is therefore inadequate. It is necessary to identify vehicles which are actually operating in violation of prescribed emission standards, and either require them to be placed in conformance with the standards or be removed from operation.

A system for remote sensing of automotive exhaust emissions is described in an article entitled "ANALYTICAL APPROACH—IR Long-Path Photometry: A Remote Sensing Tool for Automotive Emissions:, by G. Bishop et al., in Analytical Chemistry 1989, 61, 617A. An infrared beam is transmitted through the exhaust plume of an automotive vehicle to a sensor unit which includes a beam splitter which splits the beam into a carbon dioxide ($CO_2$) channel and a carbon monoxide (CO) channel.

The beam in the $CO_2$ channel passes through a bandpass filter which isolates the spectral absorption region of carbon dioxide and is incident on a photovoltaic detector. The beam in the CO channel passes through a rotating gas filter wheel, one-half of which contains a CO and hydrogen ($H_2$) mixture, and the other half of which contains nitrogen ($N_2$). From the filter wheel, the beam in the CO channel passes through another bandpass filter which isolates the spectral absorption region of carbon monoxide and is incident on another photovoltaic detector.

The output signals of the detectors vary in accordance with the transmittance of the vehicle exhaust plume at the respective wavelengths, and thereby the concentrations of CO and $CO_2$ in the plume. The $CO/H_2$ portion of the filter wheel provides a reference output, whereas the $N_2$ portion provides a carbon monoxide output.

Baseline sensor outputs are obtained with no vehicle passing through the beam, and with the beam blocked by a vehicle prior to sensing of the plume. These values are used as references for calibrating the outputs of the detectors when the plume is actually sensed. The detector outputs, which correspond to the transmittances at the respective wavelengths, are then processed in accordance with predetermined functions to determine the relative percentages of $CO_2$ and CO in the vehicle exhaust plume.

This system is said to be capable of sensing the exhaust gas composition of moving vehicles, and to be useful in identify polluting vehicles for enforcement purposes. However, it suffers from certain drawbacks.

For example, precise alignment is required to ensure that the beams in the two paths are incident on the detectors in an identical manner. A small misalignment error can seriously degrade the measurement accuracy. The two photovoltaic detectors are remote from each other, and require separate cooling units for temperature regulation. A small difference in temperature, as well as small mismatches in other characteristics of the detectors, can also seriously degrade the measurement accuracy.

The rotating filter wheel is a mechanical unit which is expensive and prone to mechanical malfunction. The concentrations of the gasses in the filter must be maintained at precise values in order to obtain accurate measurements. The system is also difficult to expand for sensing of additional pollutant species, since each new channel will require another beam splitter, detector, etc. and involve the problems described above.

Commonly assigned U.S. patent application Ser. No. 08/119,788, filed Sep. 10, 1993, entitled "Optical Sensing Apparatus For Remotely Measuring Exhaust Gas Composition of Moving Motor Vehicles" by Michael D. Jack et al. teaches an IR based system that overcomes the foregoing problems. This system employs a number of adjacently spaced photodetectors that are sensitive to different wavelengths corresponding to spectral absorption peaks of constituents of the composition of an exhaust plume, including carbon monoxide, carbon dioxide, and hydrocarbon.

However, one particularly noxious pollutant that is not sensed at all by known types of systems, or that is only inaccurately sensed, is nitric oxide (NO).

Standard infrared techniques such as FTIR fail in quantifying NO in the atmosphere because of the significant interference resulting from water absorption in absorbing bands in the region around 5.2 $\mu$m and 6.2 $\mu$m in which NO absorbs. Attempts to subtract the water absorption band are not successful due to the limited accuracy with which water absorption signature can be modeled over the entire spectral region in which FTIR, by its nature, must scan.

Alternate IR laser approaches that use overtone techniques are also not adequate, due at least in part to the requirement to compensate for the water vapor absorption, and to a requirement to provide very accurate temperature control.

An alternative approach utilizes UV absorption in the spectral region around 270 nm. Although NO absorption is strong in this spectral region, the application of this approach to moving vehicles is difficult due to interference from natural pollutants present in the automotive exhaust, i.e., the aromatics Benzene and Toluene. The multiplicity of aromatics emitted in a typical exhaust plume, and the absorption caused thereby, makes compensation for the aromatics very difficult, and also limits the accuracy of the measurement.

It should be appreciated that many of these problems are compounded when the exhaust gas pollution detection system is required to be portable, and also to be capable of being operated in less than ideal surroundings, such as when it is desired to monitor vehicles that are traveling on a roadway, such as a highway or freeway.

OBJECTS OF THIS INVENTION

It is therefore an object of this invention to provide a system for accurately quantifying an amount of NO in a gas plume that overcomes the foregoing and other problems inherent in the various approaches described above.

It is a further object of this invention to provide an IR-based system and method for accurately quantifying a concentration of NO in a gas plume, wherein the system and method compensate for ambient water vapor and also the water vapor that is present in the plume.

It is one further object of this invention to provide a sealed gas cell having a capability to vary a path length product for use in calibrating an exhaust gas emission system.

SUMMARY OF THE INVENTION

The foregoing and other problems are overcome and the objects of the invention are realized by a unique combination of infrared sensors and integrated, narrow band filters that quantitatively measure the concentration of NO in an exhaust plume, such as the exhaust plume of a moving vehicle. This invention overcomes the above-described and other limitations by utilizing narrow band measurements of limited spectral regions of the IR band which provide high absorption by NO and also high absorption by water. An algorithmic manipulation of signals derived from IR detectors, in conjunction with a reference channel, compensates for variations in an IR source, and further enables an accurate, real-time compensation for water both in the atmosphere and as emitted in the exhaust of the automobile. In this invention the water concentration as background, due to relative humidity (R.H.), and in the exhaust emitted by a vehicle is determined by measurement in an appropriate water absorption band, for example bands centered at 1998 cm$^1$ or 2003 cm$^1$, utilizing a narrow band filter which selects radiation only within a narrow spectral region that is closely adjacent to the resonant absorption peak(s) of NO.

Compensation for the presence of water vapor is provided by utilizing a lookup table that is generated by modeling and measurements. The accuracy of this lookup table technique is shown to 2% or better. With accurate compensation for absorption by the water band the final sensitivity of the system is shown to be limited only by the width of the spectral filter around the NO line. For example, with a spectral filter having a 1% width a concentration of NO that is equal to or less than 500 ppm can be detected, even with high levels of water in the exhaust and with high levels of relative humidity (up to approximately 60% R.H.).

This approach thus provides an accurate quantitative measurement of NO and water vapor using IR radiation channels in concert with narrow band filters. Narrow band compensation enables sensitivities as low as 100 ppm for automotive exhaust.

The teaching of this invention overcomes the above described deficiencies in the FTIR and UV measurement techniques, which are limited by inaccuracies due to incomplete compensation for water across the entire spectral band, and by inaccurate compensation for interfering UV absorbing species (i.e., aromatics) which cannot be compensated for a priori, respectively.

This invention thus provides in a first aspect thereof a system for detecting NO within an exhaust plume. The system includes a source for generating an optical beam and for directing the optical beam through the exhaust plume, the optical beam having wavelengths within a predetermined band of wavelengths within the infrared (IR) radiation spectrum. The system further includes a radiation sensor/filter assembly having a first channel for determining a measured NO transmission value for a first predetermined band of wavelengths; a second channel for determining a measured water transmission value for a second predetermined band of wavelengths; a third channel for determining a measured reference transmission value for a third predetermined band of wavelengths selected so as not to be significantly absorbed by the exhaust plume; and a fourth channel for determining a measured combustion by-product transmission value for a fourth predetermined band of wavelengths. A data processor is responsive to the outputs of the channels for determining an effective NO transmission value from the measured NO transmission value that is scaled by (a) the measured water transmission value, (b) a predetermined factor that compensates for absorption by water within the first predetermined band of wavelengths, and (c) the reference transmission value. The data processor is further operable for converting the effective NO transmission value to a relative NO concentration value using a predetermined calibration factor and for converting the relative NO concentration value to an actual NO concentration value utilizing the measured combustion by-product transmission value.

Further in accordance with this invention a sealed calibration cell is comprised of a housing that is divided into two compartments by a pair of IR-transparent pistons. The housing has IR-transparent windows at opposing ends thereof for permitting passage of a beam through the housing, and also through the transparent pistons. A first compartment contains a heated mixture of gases of interest (e.g., NO, $CO_2$ and $H_2O$) in a desired percentage. The mixture is maintained at a desired temperature. The concentration path length product within the sealed cell is varied by redistributing the mixture of gases between the first compartment and an attached leak tight heated gas reservoir, which may also contain a liquid water source.

Mechanical variation of the path length product through the calibration cell is accomplished by magnetically driving a first one of the pistons with a second one of the pistons through two annular permanent or electrically activated magnets. This is accomplished with a pressurized gas source that is connected to a second compartment within the housing. Pressurizing the second compartment causes a movement of the second piston which, by exerting a magnetic force on the first piston, causes a displacement of the first piston and reduces the volume of the gas mixture in the first chamber. A restoring force is applied by springs.

Other embodiments of the sealed dual-chamber cell employ a bellows to displace the first piston, or an electrostatic-actuated displacement of the first piston. A further embodiment utilizes the bellows or the electrostatic displacement in combination with an inflatable reservoir.

The use of the sealed calibration cell enables the NO, $H_2O$ and $CO_2$ detectors to be rapidly calibrated in the field. Significantly, in that the cell is a sealed system no gases are released to the atmosphere and, as a result, it is not necessary to purchase and transport replacement calibration gas canisters.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

Figure 1:
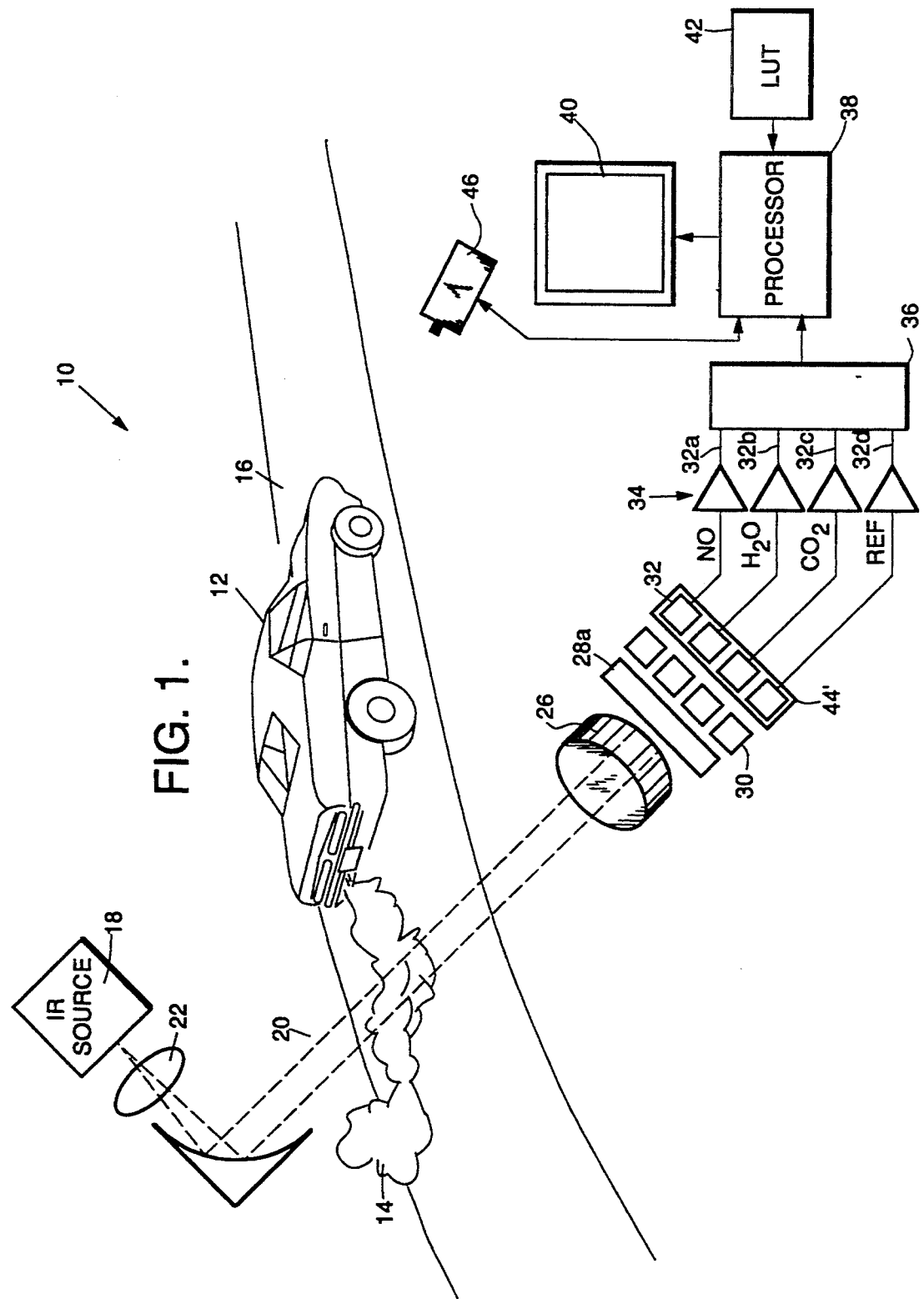
FIG. 1 is a block diagram of an exhaust gas pollution detection system that includes the multi-channel NO sensor embodiment of this invention.

FIG. 1 is an overall system diagram that illustrates multi-channel NO sensor system 10 of this invention for use with a vehicle 12 that emits an exhaust plume 14 as the vehicle travels along a roadway 16. It should be understood that the vehicle 12 does not form a part of the system 10. It should be further understood that this invention can also be used to quantify an NO emission from a smokestack, a chimney, and the like, and is not limited for use only with vehicles having internal combustion engines that emit NO as a constituent of their exhaust gas. In general, this invention is applicable to the determination of the NO concentration in a gas plume emitted by any natural or manmade source.

It should further be realized that the teaching of this invention can be employed in a stand-alone manner for quantifying only the NO concentration in an emission, or may be included within or used in conjunction with a system of the type that is described in the above-referenced commonly assigned U.S. patent application Ser. No. 08/119,788, filed Sep. 10, 1993, entitled "Optical Sensing Apparatus For Remotely Measuring Exhaust Gas Composition of Moving Motor Vehicles" by Michael D. Jack et al. As such, the disclosure of U.S. patent application Ser. No. 08/119,788, filed Sep. 10, 1993, is incorporated by reference herein in its entirety.

The system 10 includes an IR source 18, preferably a broadband IR source such as a glow bar, that has a significant IR radiation output in the range of approximately 3 micrometers to approximately 6 micrometers. The IR source 18 provides a beam 20 that may optionally be passed through a chopper 22 (nominally 200 cycles per second) and a beam former 24, such as a reflector. The beam 20 is disposed so as to pass through the exhaust gas plume 14 of the vehicle 12 when the vehicle is in motion on the roadway 16. The passage of the IR beam 20 through the exhaust gas plume 14 results in the selective partial absorption of various wavelengths within the broadband beam, the selective absorption occurring because of the presence of NO, water vapor, $CO_2$, and other molecular species within the exhaust gas.

After passing through the plume 14 the beam 20 passes through an optional IR-transparent gas cell 26 (FIG. 5), used for calibration purposes, and then through a beam integrator or diffuser 28. The diffused beam is applied to a plurality n of narrow band filters 30, where n is equal to a number of system 10 measurement channels. Each filter 30 is selected so as to pass a predetermined narrow band of wavelengths to an associated one of a plurality of IR detectors 32. Each detector 32 outputs an electrical signal to an input of a corresponding measurement channel comprised of suitable analog electronics 34 (e.g. amplifiers), an n channel analog to digital (A/D) converter 36, and a data processor 38 having an associated output device 40. The data processor 38 provides the required signal processing of the outputs from the A/D converter 36. The data processor 38 is coupled to a lookup table (LUT) 42, the use of which is described in detail below. The LUT 42 is most readily implemented as a region of memory (semiconductor and/or disk) that is accessible by the data processor 38. A suitable cooler 42, such a thermo-electric (TE) device, is employed for cooling those types of IR detectors 32 are required to be cooled to an operating point that is below ambient temperature.

In a presently preferred embodiment of this invention there are four spectral measurement channels. These are an NO spectral channel 32a (having a filter 30 with a passband centered on 5.26 $\mu$m), an $H_2O$ spectral channel 32b (having a filter 30 with a passband centered on 5.02 $\mu$m), a first reference, or $CO_2$ spectral channel 32c (having a filter 30 with a passband centered on 4.2 $\mu$m), and a second reference (REF) spectral channel 32d (having a filter 30 with a passband centered on 3.8 $\mu$m). Additional channels to measure other pollutants can also be added if desired. In general, the NO spectral channel 32a is located near resonant absorption peaks in the vicinity of 5.2 μm; the water vapor spectral channel 32b is in a region of strong water absorption where fundamental lines do not saturate; the first reference spectral channel 32c is employed for normalizing the pollutants to the normal combustion products, i.e., $CO_2$; and the second reference (REF) spectral channel 32d is provided at a region in which no atmospheric or automotive emissions gases absorb.

The REF spectral channel is provided to compensate the other three spectral channels for variations caused by: (a) fluctuations in the output of the IR source 18; (b) particulate matter in the form of road dust; and (c) particulate matter in the exhaust gas plume 14, and any other factors that may reduce the amount of illumination reaching the detectors 32. The REF spectral channel thus operates to provide a baseline output which is independent of the molecular species (NO, $H_2O$, and $CO_2$) being measured. The output of the REF spectral channel 32d is used to normalize, such as by dividing, the three molecular species spectral channels 32a–32c.

The detectors 32 are preferably comprised of high detectivity (sensitivity) materials, and are also preferably fabricated on or bonded to a common substrate. Suitable examples include, but are not limited to, photoconductive HgCdTe (TE cooled); InSb that is cooled to 77 K. (liquid nitrogen temperatures); or uncooled detectors such as those based on bolometers, thermopiles, pyroelectrics, and Pb-Salt detectors. Each detector 32 is configured with the electronics 34 for amplification and as such provides an electrical signal to one of the four spectral measurement channels. Photovoltaic detectors may also be used.

The detectors 32 are preferably optically isolated from each other with an opaque material, such as alumina, to minimize optical cross-talk. The optical filters 30 having the predetermined passbands and are preferably formed on a transparent substrate and then adhered to the elements of the detectors 32 by an optically transparent adhesive. By example, the filters 30 are formed on a substrate comprised of germanium (Ge), the filters 30 being formed as multi-layered dielectric stacks including multiple layers of zinc sulfide (ZnS).

Exemplary dimensions for each of the detectors 30 are approximately 1×1 millimeter, although the invention is not so limited. These dimensions are sufficiently large so as to accommodate the filters 32 while still achieving a high signal-to-noise ratio. The integral design of the photodetector assembly (detectors and filters) ensures that the photodetectors 32 operate isothermally, thereby eliminating inaccuracies resulting from temperature differences. If required, the temperature of the detectors 32 is regulated by the cooler 44.

The beam integrator 28 preferably includes a plano-convex lens portion 28a. A rectangular array of flat facets are formed in a convex surface of the lens 28a. The facets refract segments of light from respective portions of the incident beam 20 toward a central axis such that the refracted light segments are superimposed with each other on the photodetectors 32. The superimposed image which is incident on the detectors 32 is a homogenized or averaged image refracted from the facets, and thereby represents the average intensity of the beam 20. A converging lens may optionally be employed for reducing the size of the homogenized image on the photodetectors 32.

The principles of a preferred embodiment of the beam integrator 28 are disclosed in U.S. Pat. No. 4,195,913, entitled "OPTICAL INTEGRATION WITH SCREW SUPPORTS" issued Apr. 1, 1980 to D. Dourte. A beam integrator that is suitable for practicing the invention is commercially available from Spawr Optical Research, Inc. of Corona, Calif.

It should be realized that the configuration of the beam integrator 28 suitable for practicing the invention is not limited to the multifaceted embodiment that was just described. For example, the beam integrator 28 can be embodied by a converging or diverging lens which produces a de-focussed image of the beam 20 on the photodetectors 32. The beam integrator 36 can also be embodied using a reflective, rather than a refractive implementation.

Figure 6:
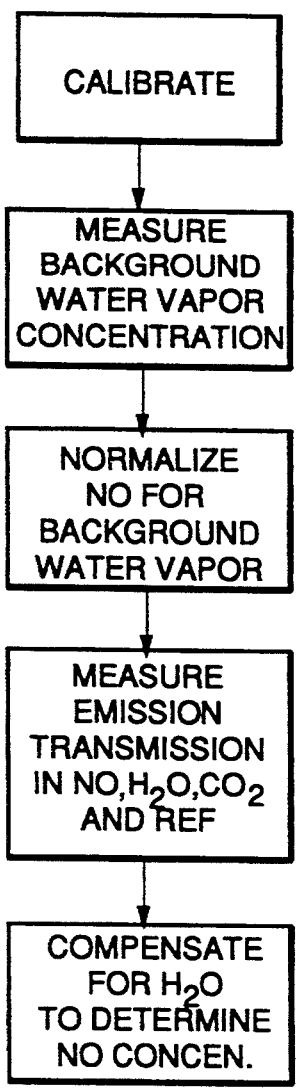
FIG. 6 is a logic flow diagram that illustrates a method of this invention for determining the NO concentration in an exhaust plume.

A method of this invention, illustrated in FIG. 6, includes the following steps: (A) calibration of the system 10 using the cell 26; (B) measurement of the background water vapor concentration utilizing the water band absorption (for example, at wavelengths such as 1998 $cm^1$ or 2023 $cm^{-1}$); (C) background normalization for water vapor absorption in the NO band; and (D) real time measurements of automotive exhaust transmission in the NO, water vapor, and $CO_2$ spectral channels 32a–32c, augmented by a next step (E) of algorithmically compensating for the water emitted by the vehicle 12 through the use of the lookup table 42. As was described above, the lookup table 42 contains entries which relate absorption by water vapor in the water spectral channel 32b to absorption by water vapor in the selected NO spectral band(s).

Figure 2:
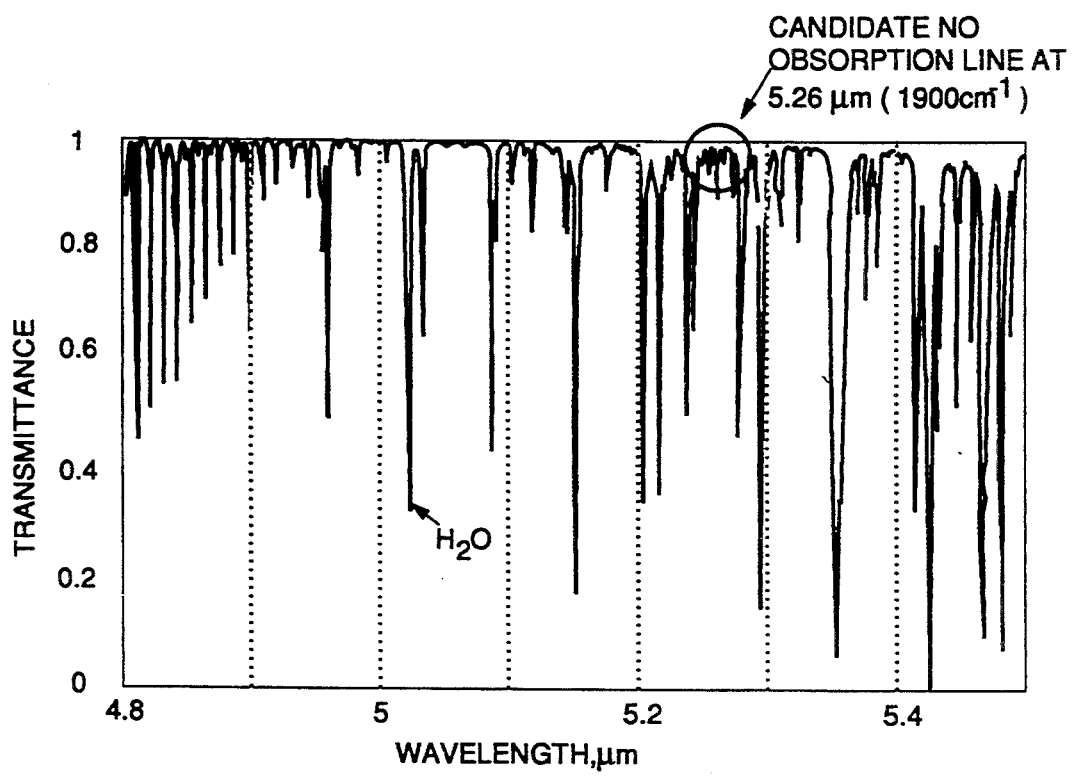
FIG. 2 graphically illustrates the close proximity of the water vapor absorption spectrum to the desired NO absorption spectrum.

In this regard FIG. 2 shows a spectral region of interest around 5.26 μm, one of the preferred NO absorption lines. The water absorption band is shown at approximately 5.02 μm. The REF region at approximately 3.8 μm is not shown.

Figure 3:
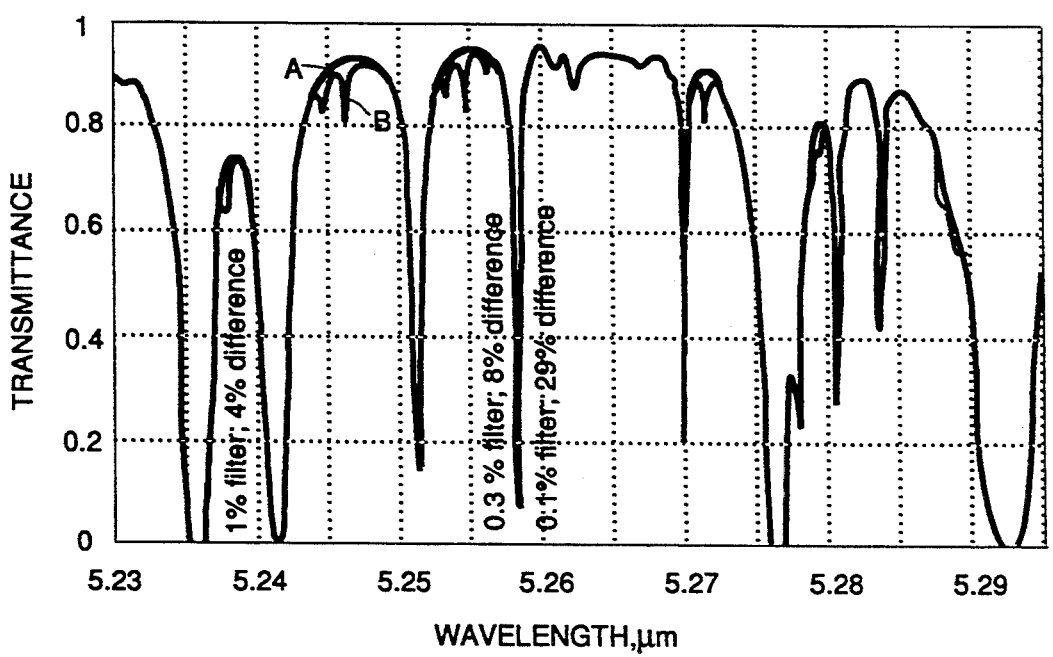
FIG. 3 graphically illustrates the effect of different ideal filters on the measurement of the NO absorption band.

FIG. 3 shows an expanded spectrum around the 5.26 μm NO line and illustrates the use of several different spectral widths (0.1%, 0.3%, and 1%) for the NO filter 30. The heavy line (designated "A") illustrates a 60% relative humidity case with zero ppm NO in the exhaust plume 14, while the lighter line (designated "B") illustrates the 60% relative humidity case with 1000 ppm NO in the exhaust plume 14. The graph of FIG. 3 assumes "perfect" passband filters 30 having vertical sides and 100% transmittance. The "percent difference" term is a measure of the effect of the NO on the area under the curve.

A fraction of NO absorption to water absorption is shown in Table 1 as a function of relative humidity and spectral passband (as determined by the particular one of the filters 30 that is utilized).

TABLE 1

Ratio of Absorption by 1000 ppm NO to Absorption by Water in a Spectral Band Around 5.2 μm as a Function of Spectral Filter Width and Relative Humidity

| Filter Width | Relative humidity at 90° F. | | | |
|---|---|---|---|---|
| | 0% | 30% | 60% | 90% |
| 0.1% | 184% | 54% | 29% | 18% |
| 0.3% | 33% | 12% | 8% | 5% |
| 1.0% | 15% | 5% | 4% | 3% |

The entries of Table 1 also take into account the presence of water vapor that is present in the exhaust gas plume 14. As shown, and for a 60% relative humidity across, by example, a 30 foot optical path length and a 1000 ppm NO concentration, the ratio of relative absorption of the water line to the relative absorption due to the NO varies from 29% for a 0.1% filter to 4% for a 1% filter. This ratio thus determines the accuracy of the field/laboratory calibration necessary to measure NO at a given sensitivity. For example, in the case of a 1% filter the ratio of integrated NO absorption to spectral water absorption is 4%. Hence with a 2% accuracy in the lookup table correction, 500 ppm of NO is the limit of detection at 60% R.H and a 30 foot spacing between the IR source 18 and the detectors 32. In contrast, with an NO filter 30 having a 0.1% passband the concentration ratio is 29%. For this case with a 2% accuracy in the lookup table correction 100 ppm of NO is the limit of detection at 60% R.H. and a 30 foot spacing. The following is an example of the $NO_x$ lookup table 42.

| % | Absorption $C_{H2O}$ (Band 1) | Transfer Function $T = \dfrac{C_{H2O} \text{ (Band 1)}}{C_{H2O} \text{ (Band 2)}}$ | Absorption $C_{H2O}$ (Band 1) |
|---|---|---|---|
| 1.0 | .0011014 | 3.205 | .00353012 |
| 2.0 | .0210755 | 3.205 | .00673933 |
| 3.0 | .0030484 | 3.205 | .00977024 |

Figure 4:
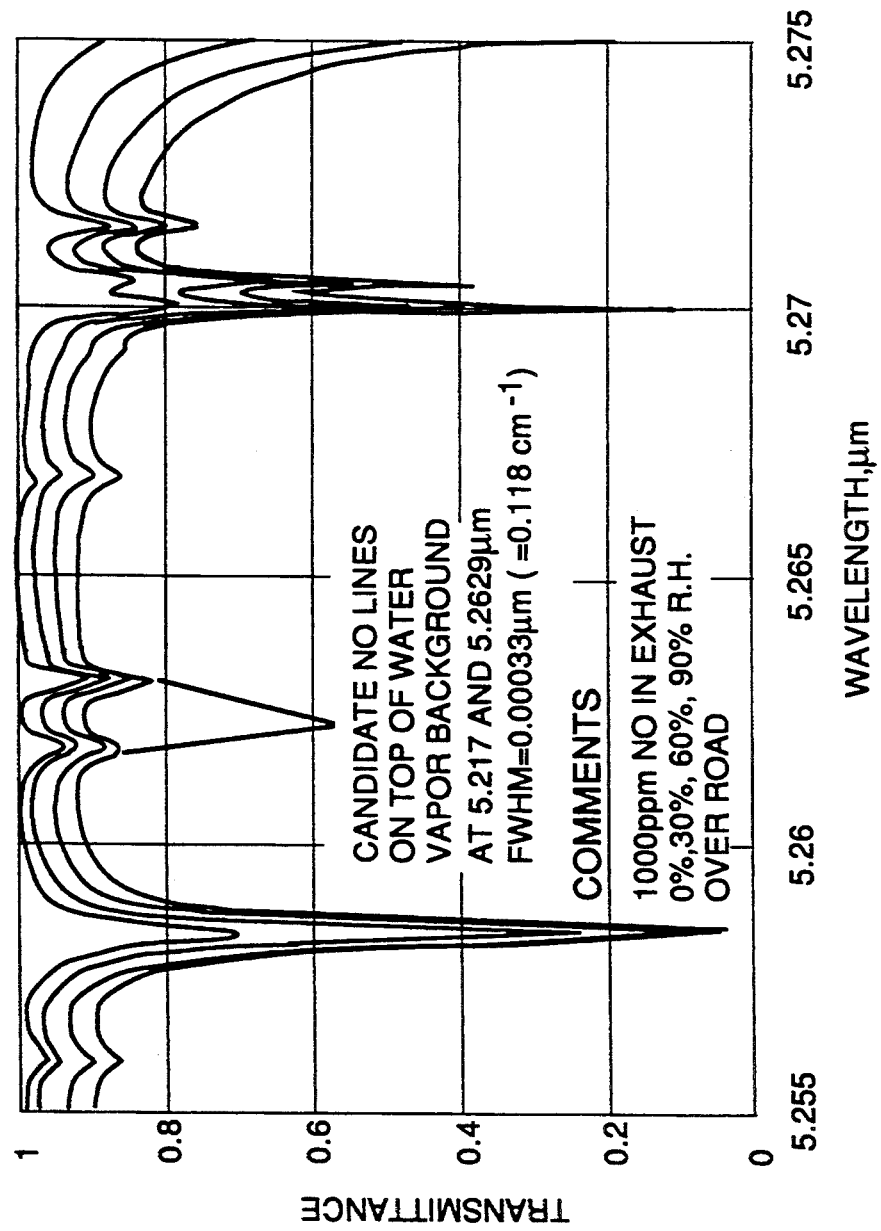
FIG. 4 graphically illustrates two candidate NO spectral lines (5.2617 $\mu$m and 5.2629 $\mu$m) atop background water vapor lines for different relative humidity levels, and makes evident a requirement to subtract the water vapor background.

The graph of FIG. 4 illustrates the importance of subtracting out or compensating for the absorption due to the water vapor background. In FIG. 4 the spectral plots for different amounts of relative humidity illustrate the monotonic offset in the NO baseline vs relative humidity. This linear shift, corresponding to a flat top absorption integral, is compensated for very accurately if a narrow band NO filter 30 is utilized.

Figure 5:
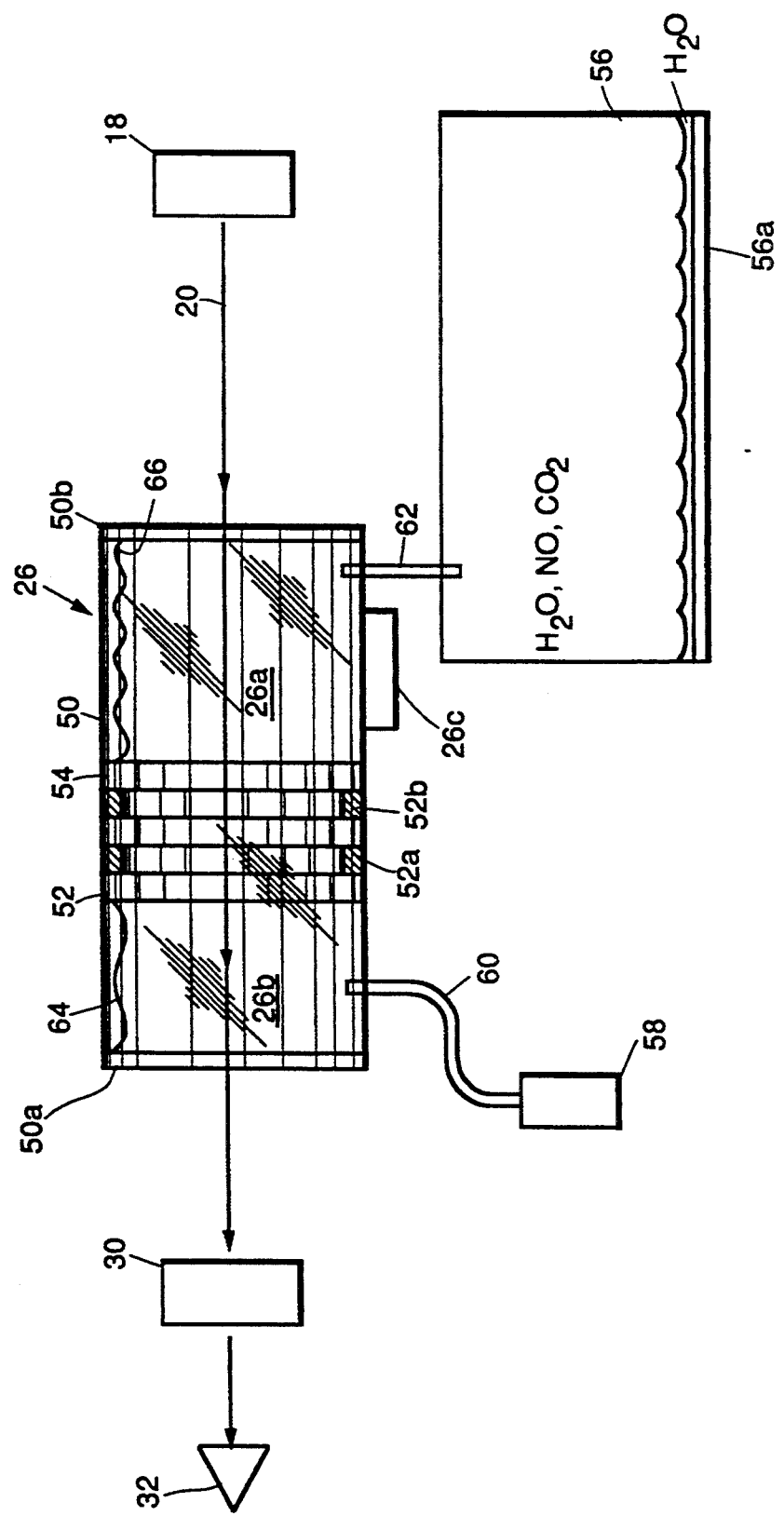
FIG. 5 is a simplified cross-sectional view (not to scale) of a gas calibration cell in accordance with an aspect of this invention.

Calibration with respect to variations in the illumination provided by the source 18 across the various detectors 32 is preferably accomplished using the heated calibration cell 26 that is depicted in FIG. 5.

In accordance with an aspect of this invention the calibration cell 26 is comprised of a housing 50 that is divided into two compartments 26a and 26b by a pair of IR-transparent pistons 52 and 54. The housing 50 has IR-transparent windows 50a and 50b at opposing ends thereof for permitting passage of the beam 20 through the housing, and also through the transparent pistons 52 and 54. The compartment 26b contains a heated mixture of gases of interest (.e.g., NO, $CO_2$ and $H_2O$) in a desired percentage such as, by example, 2%, 15% and 15%, respectively. Other gases, such as CO (15%) are also typically provided, as are various hydrocarbons (2%). The calibration gas mixture is maintained at a temperature of, by example, approximately 100 C. The concentration path length product within the sealed cell 26 is varied by redistributing the mixture of gases between the optically transparent compartment 26b and an attached leak tight gas reservoir 56, which may also contain a liquid water source. The reservoir 56 includes a heater 56a, and the compartment 26a also includes a heater 26c for maintaining the desired temperature.

Mechanical variation of the path length through the cell 26 is accomplished by magnetically driving the piston 54 with the piston 52 through two annular permanent or electrically activated magnets (52a and 52b). This is accomplished with a pressurized gas (air) tank 58 and a conduit 60 which is connected to the chamber 26a. Pressurizing the compartment 26a causes the piston 52 to move to the right in the drawing, thereby exerting a repelling magnetic force on the piston 54 through the magnets 52a and 52b. This causes the piston 54 to also move to the right, thereby reducing the volume of the gas mixture in the chamber 26a through conduit 62 and sealed reservoir 56, and thus varying the path length product within the cell 26. A restoring force is applied by compression springs 64 and 66.

The use of the calibration cell 26 enables the NO, $H_2O$ and $CO_2$ detectors 32 to be rapidly calibrated in the field with respect to each other. Significantly, in that the cell 26 is a sealed system no gases are released to the atmosphere and, as a result, it is not necessary to purchase and transport replacement calibration gas canisters. In that NO is considered to be a toxic substance, this is a significant advantage.

During the actual measurement of one or more exhaust plumes the calibration cell 26 can be removed from the beam. Alternately, the calibration cell 26 can be controlled to reduce the volume of the chamber 26a to zero. The minimal absorption of the beam 20 as it passes through the cell 26 is compensated by the REF spectral channel measurement, as was previously described.

The use of other approaches, such as a bellows or rotary to linear feedthroughs, are also within the scope of this invention.

Figure 9A:
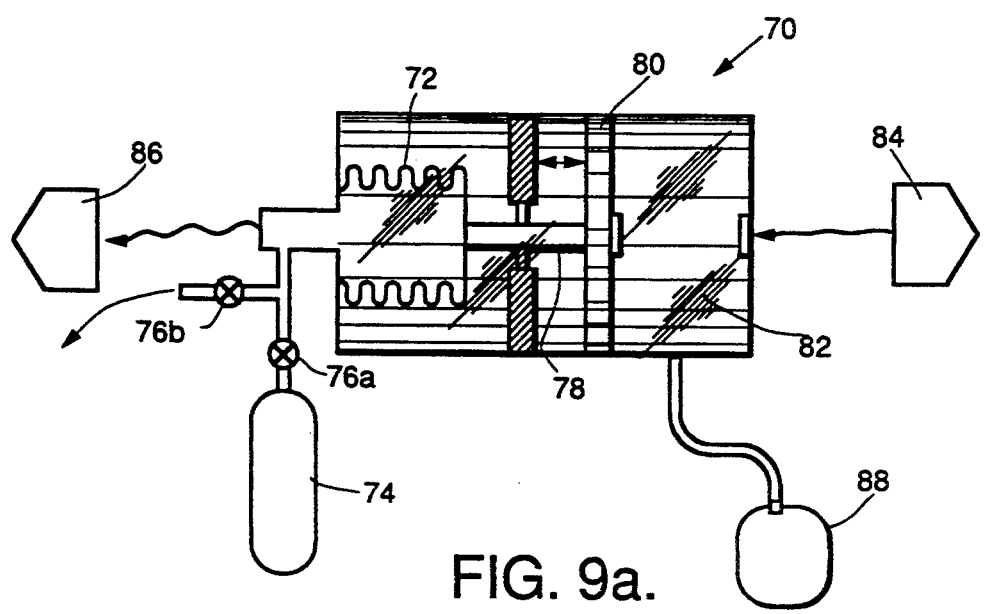
FIGS. 9A-9C each illustrate a cross-sectional view of a different embodiment of a sealed calibration cell.
Figure 9B:
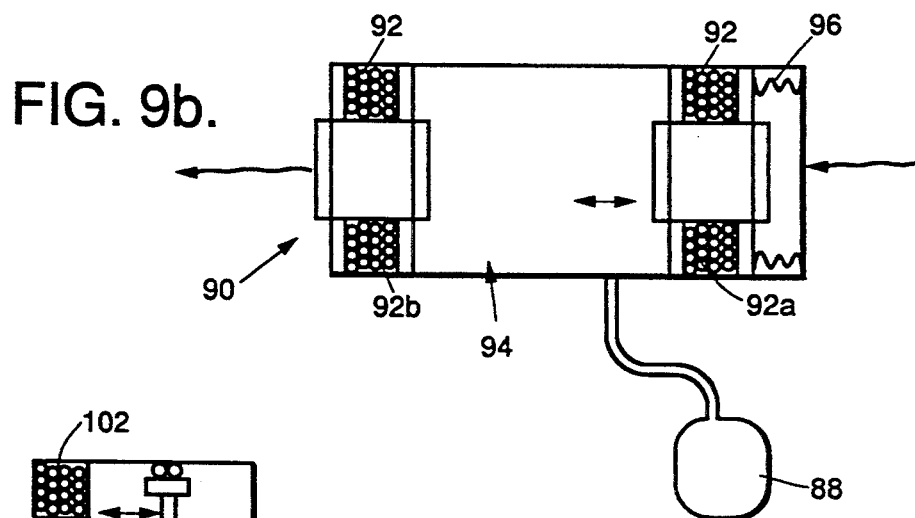
Figure 9C:
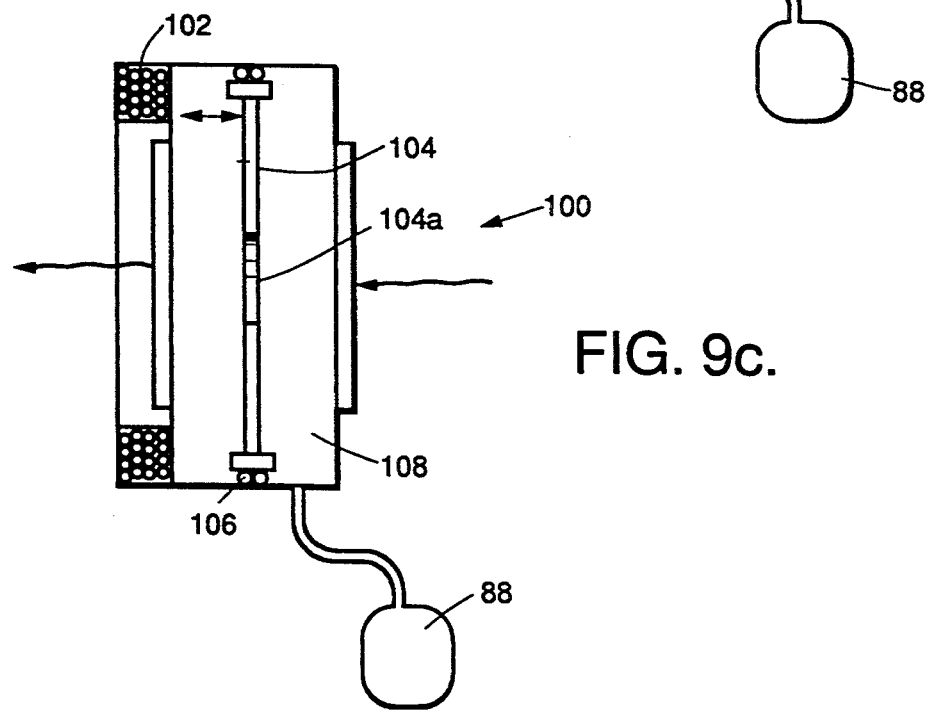

As an example, reference is made to FIGS. 9A-9C for illustrating further embodiments of the calibration cell.

FIG. 9A illustrates a calibration cell 70 that includes a bellows 72 that is driven from a compressed air cylinder 74 through valves 76a and 76b. Valve 76b is opened to vent the bellows 72. The bellows 72 drives, through an IR transparent coupling 78, a piston 80. The piston 80 operates to change the pathlength through a compartment 82 for radiation propagating from a source 84 to a detector 86. This embodiment includes an expandable reservoir 88 for providing the desired gas mixture and also, preferably, water vapor to the compartment 82.

FIG. 9B shows an embodiment of a calibration cell 90 that employs electromagnets 92 to change the optical pathlength through a compartment 94. The electromagnet assembly 92a is capable of motion and is controllably attracted and repelled by the electromagnet 92b. The movable electromagnet assembly 92a is biased with springs 96. The expandable reservoir 88 is used, as in the embodiment of FIG. 9A, to provide the desired gas mixture to the compartment 94.

FIG. 9C shows an embodiment of a calibration cell 100 that operates with a polarity reversible electromagnet 102 and an annular permanent magnet 104. By example, the annular permanent magnet 104 may be a magnetized samarium cobalt disk having a centrally disposed IR transparent window 104. The magnet 104 is contained within a bearing assembly 106. Reversing the polarity of the electromagnet 102 causes a motion of the magnet 104 which varies the optical pathlength through a gas containing compartment 108. The compartment 108 is also coupled to the expandable reservoir 88, as in the embodiments 9A and 9B.

In the operation of the system 10 a signal processing routine executed by the data processor 38 of FIG. 1 carries out the method depicted in FIG. 6. The data processor normalizes the signal in the NO band by both the transmission determined in the REF channel and the transmission determined in the water vapor channel, converted by the use of the look up table 42 to a residual transmission of water in the NO band. This normalization is performed continuously both for background measurements and for dynamic emission measurements using the functional expression:

$$T(NO)_{eff} = T(NO)/(T(H_2O) \times \{Lookup(H_2O \text{ band to NO band})\} \times T(REF)),$$

where $T(NO)_{eff}$ is the effective NO transmission, T(NO) is the measured NO transmission, $T(H_2O)$ is the measured water transmission, Lookup($H_2O$ band to NO band) is a predetermined water/NO absorption correction obtained from the lookup table 42, and T(REF) is the measured REF spectral channel transmission.

The relative NO concentration in the exhaust plume 14 is derived from the foregoing expression using the transmission versus concentration of the NO detector 32 established during factory calibration and as updated during the field calibration utilizing the cell 26. The actual NO concentration in the exhaust gas plume 14 is determined as the ratio of NO in the plume 14 to the measured concentration of the $CO_2$ in the plume, multiplied by the relative concentration of $CO_2$ in the exhaust as determined using an effective C:H ratio for an "average" fuel. For example, a $CO_2$ concentration of 15% is a reasonable value for an exhaust plume that results from the combustion of an "average" fuel.

In other words, the method first determines the effective NO transmission from the measured NO transmission scaled by (a) the measured water transmission, (b) the lookup table factor, and (c) the REF channel output which compensates for particulates, dust and the like that may obscure the beam 20. Having determined the effective NO transmission, this value is converted to a relative NO concentration using the results obtained from factory calibrations, as last updated by the use of the known NO concentration within the calibration cell 26. Having determined the relative NO concentration, this value is converted to an actual NO concentration by using the measured $CO_2$ concentration, and assuming the effective C:H ratio for a typical fuel.

Figure 8:
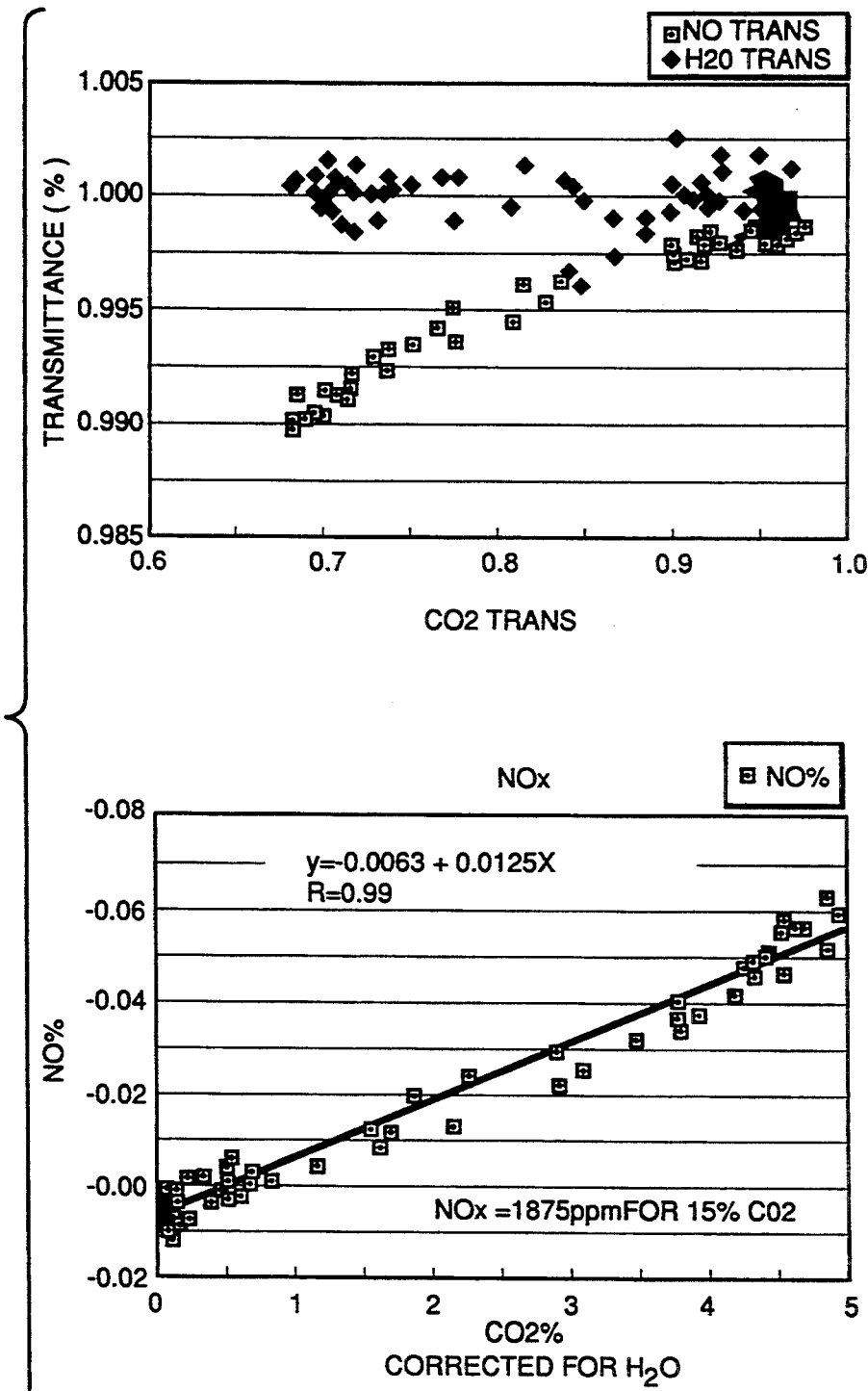
FIGS. 8A and 8B are graphs illustrating the use of this invention in measuring an emission from a high-emitting vehicle (1875 ppm) and a relatively low emitting vehicle, respectively, with FIG. 8B further showing the compensation for water vapor in the exhaust plume.
Figure 8:
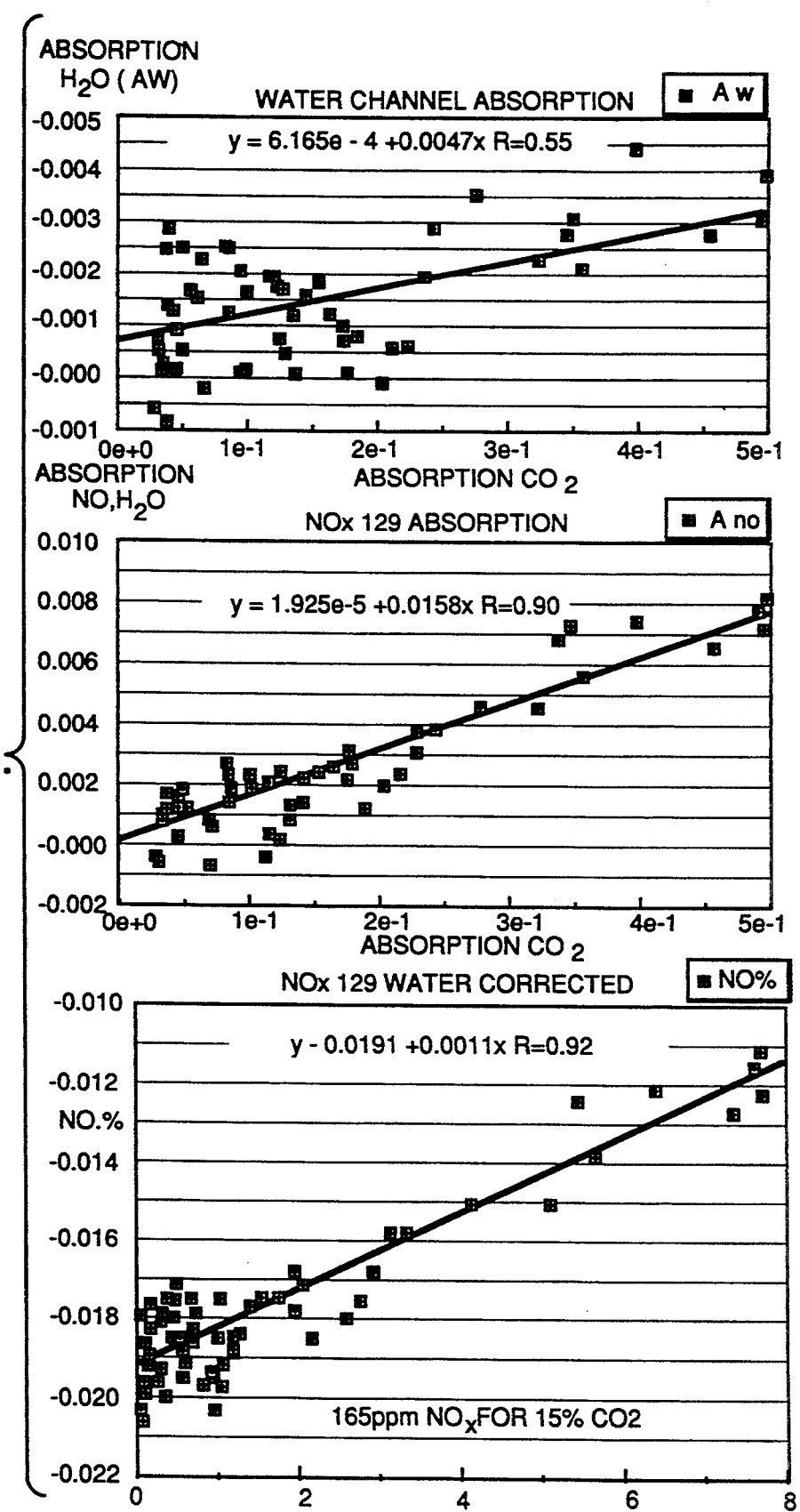

FIGS. 8A and 8B are graphs illustrating the use of this invention in measuring an emission from a high-emitting vehicle (1875 ppm) and a relatively low emitting vehicle, respectively, with FIG. 8B further showing the compensation for water vapor in the exhaust plume.

Figure 7:
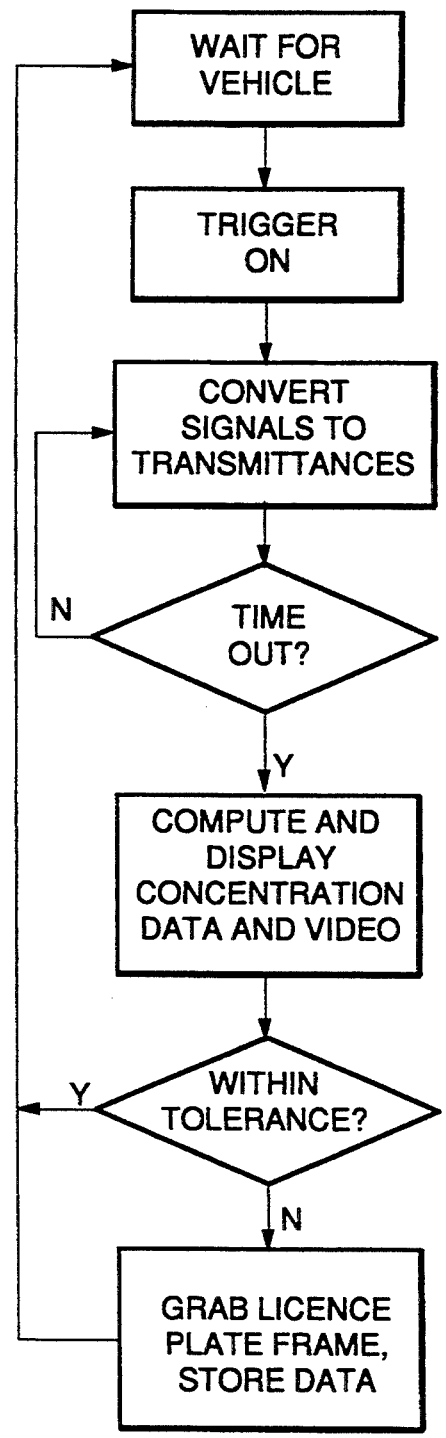
FIG. 7 is a logic flow diagram that illustrates a method of this invention for monitoring the exhaust emissions of vehicles traveling on a roadway.

The overall operation of the system 10 is illustrated in the flowchart of FIG. 7. The system 10 is suitable for attended operation or for unattended operation, once the components have been set up and calibrated.

The system 10 waits for a vehicle 12 to pass through the beam 20. This is indicated by a sharp drop in amplitudes of the output signals of the photodetectors 32 when the vehicle 12 blocks the beam 20. This generates a trigger which initiates measurement of the NO concentration of the vehicle exhaust plume 14.

The signal amplitudes output by the detectors 32 will increase sharply when the rear end of the vehicle 12 clears the beam 20. This indicates that the beam 20 is unblocked and is propagating through the exhaust plume 14 of the vehicle 12.

The data processor 38 integrates the output signals from the detectors 32 during the intervals that the photodetectors 32 are unblocked by the chopper 22. In this manner the outputs of the photodetectors 32 are periodically sampled and processed.

The data processor 38 then computes the composition of the plume 14 in terms of at least the percentage or concentration of the constituent NO, based on the amplitudes of the signals from the photodetectors 32.

This data may be displayed, together with the video from the camera 46, on the monitor 40 as illustrated in FIG. 1. This operation is performed for a predetermined length of time, for example one-half second, which is sufficient for the system 10 to produce an accurate measurement. The data processor 38 then determines if the composition is within specified regulatory tolerances. If so, the apparatus 10 resets and waits for the next vehicle. If not, indicating that the vehicle 12 is producing excessive pollution, the data processor 38 inputs a frame of video from the camera 46, the video including an identifying characteristic of the vehicle 12, such as an image of the license plate, superimposes at least the NO concentration data on the video frame, and stores the combined video and data frame in a mass storage device such as a hard drive.

The data can be retrieved at a later time for enforcement use, such as sending a notice of violation to the owner of the vehicle. It is also within the scope of the invention to store a combined video and data frame for every vehicle which passes through the beam 20, rather then just polluting vehicles, for applications such as generating a database of exhaust gas composition for different types and makes of vehicles.

A number of modifications can be made to the system 10 which will fall within the scope of this invention. As an example, the calibration cell 26 may not be required if the initial laboratory calibration of the detectors is considered to be sufficient. Also, other detectors can also be employed, with suitable filters, to measure other molecular species of interest, such as CO and/or hydrocarbons.

Thus, while the invention has been particularly shown and described with respect to a preferred embodiment thereof, it will be understood by those skilled in the art that changes in form and details may be made therein without departing from the scope and spirit of the invention.

What is claimed is:

1. A system for determining a concentration of NO in an exhaust plume, comprising:

a source of electromagnetic radiation for directing radiation having a plurality of wavelengths along an optical path that passes through the plume;

first sensor means having an output for indicating an amount of absorption of the radiation, within a band of first wavelengths, that is due to the presence of NO in the plume;

second sensor means having an output for indicating an amount of absorption of the radiation, within a band of second wavelengths, that is due to the presence of water along the optical path; and means, having inputs coupled to the outputs of said first sensor means and said second sensor means, for compensating the indicated absorption within the first band of wavelengths in accordance with the indicated absorption within the second band of wavelengths and in accordance with a predetermined NO absorption modifying factor.

2. A system as set forth in claim 1 wherein the predetermined NO absorption modifying factor is stored within a lookup table means.

3. A system as set forth in claim 1 and further comprising:

third sensor means having an output for indicating an amount of absorption of the radiation, within a band of third wavelengths, that is due to the presence of a predetermined combustion product in the plume; and wherein said determining means includes means for determining a concentration of NO in the plume from the compensated indicated absorption within the first band of wavelengths and in accordance with the indication from said output of said third sensor means.

4. A system as set forth in claim 3 wherein the predetermined combustion product is $CO_2$.

5. A system as set forth in claim 3 and further comprising a calibration cell that is interposed between said first, second and third sensor means and the plume such that the radiation passes through said calibration cell, said calibration cell comprising a compartment having a volume that contains NO, water, and at least one combustion product in a predetermined concentration, said calibration cell further including means for controllably varying the volume of said compartment.

6. A system as set forth in claim 1 and further comprising:
fourth sensor means having an output for indicating a variation in the intensity of the radiation within a band of fourth wavelengths that are selected so as not to be significantly absorbed within the plume; and wherein
said determining means is responsive to said output of said fourth sensor means for compensating the indicated absorption within the first band of wavelengths and also the indicated absorption within the second band of wavelengths in accordance with the indication output by said fourth sensor means.

7. A system as set forth in claim 1 wherein said source of electromagnetic radiation outputs radiation within a band of wavelengths that includes a band from approximately 3 microns to approximately 6 microns, wherein said first band of wavelengths includes a wavelength of approximately 5.26 microns, and wherein said second band of wavelengths includes a wavelength of approximately 5.02 microns.

8. A system as set forth in claim 1 wherein said first sensor means includes a first photodetector and a first filter interposed between the first photodetector and the plume, wherein the first filter has a wavelength passband of predetermined width that includes a wavelength of 5.26 microns; and wherein said second sensor means includes a second photodetector and a second filter interposed between the second photodetector and the plume, wherein the second filter has a wavelength passband of predetermined width that includes a wavelength of 5.02 microns.

9. A system as set forth in claim 8 and further comprising means for homogenizing the radiation after the radiation passes through the plume, said homogenizing means being interposed between each of said first and second filters and said plume.

10. A method for determining a concentration of NO in an exhaust plume, comprising the steps of:
passing an optical beam through an exhaust plume, the optical beam having wavelengths within a predetermined band of wavelengths within the infrared radiation spectrum;
determining a measured NO transmission value for a first predetermined band of wavelengths;
determining a measured water transmission value for a second predetermined band of wavelengths;
determining a measured reference transmission value for a third predetermined band of wavelengths selected so as not to be significantly absorbed by the exhaust plume;
determining a measured combustion by-product transmission value for a fourth predetermined band of wavelengths;
determining an effective NO transmission value from the measured NO transmission value that is scaled by (a) the measured water transmission value, (b) a predetermined factor that compensates for absorption by water within the first predetermined band of wavelengths, and (c) the reference transmission value;
converting the effective NO transmission value to a relative NO concentration value using a predetermined calibration factor; and
converting the relative NO concentration value to an actual NO concentration value utilizing the measured combustion by-product transmission value.

11. A method as set forth in claim 10 wherein the predetermined combustion by-product is $CO_2$.

12. A method as set forth in claim 10 wherein the exhaust plume is generated by a motor vehicle, and further comprising the steps of:
comparing the actual NO concentration value to a predetermined value; and, if the actual NO concentration value exceeds the predetermined value,
recording an identifying characteristic of the motor vehicle in association with the actual NO concentration value.

13. A method as set forth in claim 10 wherein the step of determining an effective NO transmission value $(T(NO)_{eff})$ is accomplished in accordance with:

$$T(NO)_{eff} = T(NO)/(T(H_2O) \times \{\text{Lookup}(H_2O \text{ band to NO band})\} \times T(REF)),$$

where, $T(NO)$ is the measured NO transmission value, $T(H_2O)$ is the measured water transmission value, Lookup($H_2O$ band to NO band) is a predetermined water/NO absorption correction, and $T(REF)$ is the measured reference transmission value for the third predetermined band of wavelengths.

14. A system for detecting at least one predetermined pollutant within an exhaust plume, comprising:
means for generating an optical beam and for directing the optical beam through an exhaust plume, the optical beam having wavelengths within a predetermined band of wavelengths within the infrared radiation spectrum;
first means for determining a measured NO transmission value for a first predetermined band of wavelengths;
second means for determining a measured water transmission value for a second predetermined band of wavelengths;
third means for determining a measured reference transmission value for a third predetermined band of wavelengths selected so as not to be significantly absorbed by the exhaust plume;
fourth means for determining a measured combustion by-product transmission value for a fourth predetermined band of wavelengths; and
a data processor having inputs coupled to an output of each of said first, second, third and fourth determining means, said data processor being responsive to said outputs for determining an effective NO transmission value from the measured NO transmission value that is scaled by (a) the measured water transmission value, (b) a predetermined factor that compensates for absorption by water within the first predetermined band of wavelengths, and (c) the reference transmission value;

said data processor including means for converting the effecting NO transmission value to a relative NO concentration value using a predetermined calibration factor; and means for converting the relative NO concentration value to an actual NO concentration value utilizing the measured combustion by-product transmission value.

15. A system as set forth in claim 14 wherein the predetermined combustion by-product is $CO_2$.

16. A system as set forth in claim 14 wherein the exhaust plume is generated by a motor vehicle, and wherein said data processor is operable for comparing the actual NO concentration value to a predetermined value; and, if the actual NO concentration value exceeds the predetermined value, for recording an identifying characteristic of the motor vehicle in association with the actual NO concentration value.

17. A system as set forth in claim 14 wherein said first determining means includes a first photodetector and a first filter interposed between the first photodetector and the plume, wherein the first filter has a wavelength passband of predetermined width that includes a wavelength that is strongly absorbed by NO.

18. A system as set forth in claim 14 wherein said first determining means includes a first photodetector and a first filter interposed between the first photodetector and the plume, wherein the first filter has a wavelength passband of predetermined width that includes a wavelength of 5.265 microns; and wherein said second determining means includes a second photodetector and a second filter interposed between the second photodetector and the plume, wherein the second filter has a wavelength passband of predetermined width that includes a wavelength of 5.02 microns.

19. A system as set forth in claim 18 and further comprising means for homogenizing the radiation after the radiation passes through the plume, said homogenizing means being interposed between each of said first and second filters and said plume.

20. A system as set forth in claim 14 and further comprising a calibration cell that is interposed between said first, second, third and fourth sensor means and the plume such that the radiation passes through said calibration cell, said calibration cell comprising a compartment having a volume that contains NO, water, and at least one combustion product in a predetermined concentration, said calibration cell further including means for controllably varying the volume of said compartment.

21. A calibration cell for use in calibrating a pollution monitoring system, comprising:

a sealed housing having a plurality of compartments including a first compartment and a second compartment, said first and second compartments being separated by a movable partition;

means for causing a movement of said partition, the movement causing a volume of said first compartment to increase while simultaneously causing a volume of said second compartment to decrease;

a sealed reservoir coupled to said second compartment whereby a gas mixture is enabled to flow between said reservoir and said second compartment, said gas mixture including a plurality of by-products of combustion of a fuel; wherein at least a portion of said housing and said partition are substantially transparent to a beam of electromagnetic radiation having wavelengths within a band of wavelengths employed by a pollution monitoring system such that the beam is enabled to pass through said first compartment, said second compartment, the gas mixture contained within said second compartment, and through said partition.

22. A calibration cell as set forth in claim 21 wherein said partition is comprised of a first piston and a second piston, said first and second pistons each comprising a magnetic portion arranged so that a movement of said first piston causes a corresponding movement of said second piston due to a repelling force exerted by said magnetic portions.

23. A calibration cell as set forth in claim 21 wherein said gas mixture is comprised of predetermined percentages of at least NO, $H_2O$, and $CO_2$.

24. A calibration cell as set forth in claim 21 wherein said means for causing a movement of said partition includes means for varying a gas pressure within said calibration cell, the variation in the gas pressure causing a motion of said partition.

* * * * *